`United States Patent` [19]

Nesvadba

[11] Patent Number: 5,252,643
[45] Date of Patent: Oct. 12, 1993

[54] THIOMETHYLATED BENZOFURAN-2-ONES

[75] Inventor: Peter Nesvadba, Marly, Switzerland

[73] Assignee: Ciba-Geigy Corporation, Ardsley, N.Y.

[21] Appl. No.: 903,647

[22] Filed: Jun. 24, 1992

[30] Foreign Application Priority Data

Jul. 1, 1991 [CH] Switzerland ............... 1934/91

[51] Int. Cl.$^5$ .................. C07D 307/83; C08K 5/15
[52] U.S. Cl. ................... 524/111; 549/305
[58] Field of Search .............. 568/67; 549/305; 524/111, 331

[56] References Cited

U.S. PATENT DOCUMENTS 3,553,270  1/1971  Wollensak et al. ............ 524/331
4,325,863  4/1982  Hinsken et al. ................ 524/94

FOREIGN PATENT DOCUMENTS 0146269    6/1984   European Pat. Off. .
0415887    3/1991   European Pat. Off. .
2944295    5/1980   Fed. Rep. of Germany .
50-158639 12/1975   Japan .
61-138648  6/1986   Japan .
2034308    6/1980   United Kingdom .

OTHER PUBLICATIONS

D. J. R. Massy, Synthesis, 1987, 589–603.
J. Chem. Soc. 1956, 1622.

Primary Examiner—Veronica P. Hoke
Attorney, Agent, or Firm—Luther A. R. Hall

[57] ABSTRACT

Compounds which are benzofuran-2-ones having two organothiomethyl substituents directly attached to the benzo ring are suitable for stabilizing organic materials against thermal, oxidative or light-induced degradation.

12 Claims, No Drawings

THIOMETHYLATED BENZOFURAN-2-ONES

The present invention relates to novel thiomethylated benzofuran-2-ones, to a novel process for their preparation, to the use of these compounds for stabilising organic materials and to the organic material stabilised therewith.

Benzofuran-2-ones are disclosed, inter alia, in U.S. Pat. No. 4,325,863 and EP-A-415 887. The use of these compounds for stabilising organic materials is also described in these patent specifications.

The invention provides compounds of formula (1)

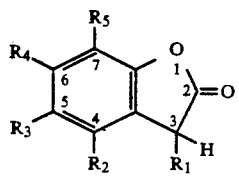

wherein $R_1$ is phenyl or phenyl which is substituted by $C_1$-$C_{18}$alkyl, $C_1$-$C_{18}$alkoxy, $C_3$-$C_{18}$alkenyloxy, benzyloxy, $C_1$-$C_{18}$alkanoyloxy, hydroxy or halogen, $R_2$ and $R_4$ are each independently of the other hydrogen or $C_1$-$C_4$alkyl, $R_4$ and $R_5$, together with the linking carbon atoms, form a phenyl ring, and $R_3$ and $R_5$ are each independently of the other hydrogen, $C_1$-$C_{18}$alkyl, $C_5$-$C_{18}$cycloalkyl, benzyl, phenyl or a radical of formula —$CH_2$—$S$—$R_6$, wherein $R_6$ is $C_1$-$C_{18}$alkyl, $C_5$-$C_{18}$cycloalkyl, benzyl, phenyl or a radical of formula —$CH_2$—$CO_2R_7$ or —$C_2H_4$—$O$—$R_8$, wherein $R_7$ is hydrogen or $C_1$-$C_{18}$alkyl and $R_8$ is hydrogen or $C_2$-$C_{19}$alkanoyl, with the proviso that at least one of the substituents $R_3$ and $R_5$ is a radical of formula —$CH_2$—$S$—$R_6$ and that the compounds of formula (2),

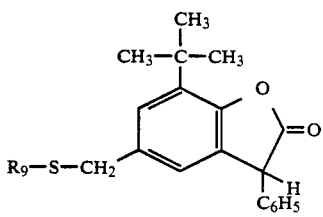

wherein $R_9$ is dodecyl or phenyl, are excluded.

Alkyl substituents of the compounds of formula (1) contain 1 to 4 and 1 to 18 carbon atoms. Suitable alkyl radicals are typically methyl, ethyl, propyl, butyl, hexyl, octyl, nonyl, undecyl, dodecyl, hexadecyl, octadecyl and corresponding branched isomers.

Alkoxy containing up to 18 carbon atoms is a branched or unbranched radical and may typically be methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy.

Alkenyloxy of 3 to 18 carbon atoms is a branched or unbranched radical and is typically propenyloxy, 2-butenyloxy, 3-butenyloxy, isobutenyloxy, n-2,4-pentadienyloxy, 3-methyl-2-butenyloxy, n-2-octenyloxy, n-2-dodecenyloxy, isododecenyloxy, oleyloxy, n-2-octadecenyloxy or n-4-octadecenyloxy.

Alkanoyloxy containing up to 18 carbon atoms is a branched or unbranched radical and is typically formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy or octadecanoyloxy.

Halogen will be taken to mean chloro, bromo or iodo, preferably chloro.

$C_5$-$C_8$Cycloalkyl is typically cyclopentyl, cyclohexyl, cycloheptyl or cyclooctyl. Cyclohexyl is the preferred meaning.

Alkanoyl of 2 to 19 carbon atoms is a branched or unbranched radical and is typically acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl.

A preferred object of the invention is the provision of compounds of formula (1), wherein $R_1$ is phenyl or phenyl which is substituted by $C_1$-$C_4$alkyl, $C_1$-$C_4$alkoxy, $C_3$-$C_4$alkenyloxy, benzyloxy, hydroxy, $C_1$-$C_5$alkanoyloxy or chloro.

Also preferred are compounds of formula (1), wherein $R_1$ is phenyl or phenyl which is substituted by $C_1$-$C_4$alkyl, $C_1$-$C_4$alkoxy, $C_3$-$C_4$alkenyloxy, benzyloxy, hydroxy, $C_1$-$C_5$alkanoyloxy or chloro.

A further preferred object of the invention is the provision of compounds of formula (1), wherein, if $R_3$ is a radical of formula —$CH_2$—$S$—$R_6$ and $R_6$ is $C_1$-$C_{18}$alkyl or phenyl, $R_5$ is not $C_1$-$C_{18}$alkyl.

More preferred compounds of formula (1) are those wherein, if $R_3$ is a radical of formula —$CH_2$—$S$—$R_6$, $R_6$ is not $C_1$-$C_{18}$alkyl or phenyl.

Still more preferred compounds of formula (1) are those wherein, if $R_3$ is a radical of formula —$CH_2$—$S$—$R_6$ and $R_6$ is $C_1$-$C_{18}$alkyl or phenyl, $R_5$ is a radical of formula —$CH_2$—$S$—$R_6$.

Particularly interesting compounds of formula (1) are those wherein the substituents $R_3$ and $R_5$ are a radical of formula —$CH_2$—$S$—$R_6$.

It is a particularly preferred object of the invention to provide compounds of formula (1), wherein $R_3$ and $R_5$ are each independently of the other hydrogen, $C_1$-$C_{12}$alkyl, cyclohexyl, phenyl or a radical of formula —$CH_2$—$S$—$R_6$, wherein $R_6$ is $C_8$-$C_{18}$alkyl, cyclohexyl, benzyl, phenyl, a radical of formula —$CH_2$—$CO_2R_7$, wherein $R_7$ is $C_{12}$-$C_{18}$alkyl, or a radical of formula —$C_2H_4$—$O$—$R_8$, wherein $R_8$ is hydrogen or $C_{13}$-$C_{19}$alkanoyl.

It is also a particularly preferred object of the invention to provide compounds of formula (1), wherein $R_1$ is phenyl or phenyl which is substituted by $C_1$-$C_4$alkyl or $C_1$-$C_4$alkoxy, $R_2$ and $R_4$ are hydrogen or $R_4$ and $R_5$, together with the linking carbon atoms, form a phenyl ring, and $R_3$ and $R_5$ are each independently of the other hydrogen, $C_1$-$C_4$alkyl, phenyl or a radical of formula —$CH_2$—$S$—$R_6$, wherein $R_6$ is $C_8$-$C_{12}$alkyl, benzyl, phenyl, a radical of formula —$CH_2$—$CO_2R_7$, wherein $R_7$ is hydrogen or $C_{12}$-$C_{18}$alkyl, or a radical of formula —$C_2H_4$—$O$—$R_8$, wherein $R_8$ is hydrogen or $C_{13}$-$C_{19}$alkanoyl.

Also very particularly preferred are compounds of formula (1), wherein $R_3$ and $R_5$ are each independently of the other hydrogen, $C_1$-$C_4$alkyl or a radical of formula —$CH_2$—$S$—$R_6$, wherein $R_6$ is $C_8$-$C_{12}$alkyl or benzyl.

The novel process for the preparation of the thiomethylated benzofuranones of formula (1) comprises starting from compounds of formula

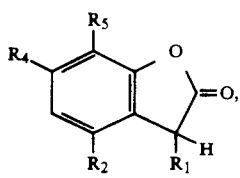
(3)

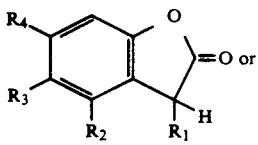
(4)

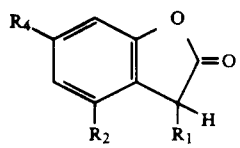
(5)

wherein at least one of the positions 5 or 7 in the benzofuranone system is hydrogen. By using suitable stoichiometric amounts it is possible to substitute the compounds of formula (1) by one or two —$CH_2$—S—$R_6$— groups in these positions. The entire reaction of these starting benzofuranones to give the compounds of formula (1) is preferably carried out in aqueous medium. It has also been found useful to carry out the reaction at boiling temperature.

In a first step (a) the compounds of formula (3), (4) or (5) are reacted with an aqueous base, conveniently sodium or potassium hydroxide and aqueous sodium carbonate solution. This treatment of the starting compounds with a base leads to a ring opening in accordance with the scheme:

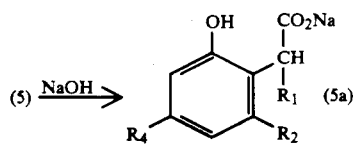

The compound of formula (5a) is (b) thiomethylated, without isolation, with formaldehyde and a mercaptan of formula $R_6$-SH in 5- and/or 7-position to the compound of formula (5b), which is then (c) subjected to an acid cyclisation in accordance with the scheme:

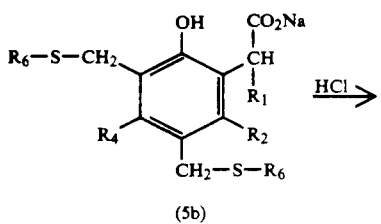

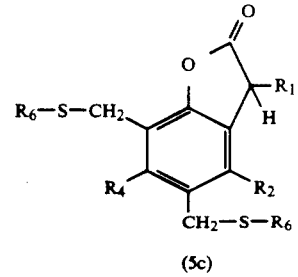
(5c)

In addition to aqueous hydrochloric acid, it is also possible to use in step (c) e.g. aqueous sulfuric or phosphoric acid.

The starting compounds of formulae (3) to (5) can be prepared, inter alia, by the method disclosed in U.S. Pat. No. 4,325,863 mentioned above, by heating appropriate phenols and mandelic acid derivatives with each other. The compounds so prepared do not need to be isolated if they are to be converted into the compounds of the invention.

Mandelic acids which are substituted at the phenyl ring are known in the literature and may conveniently be prepared by the method described by W. Bradley et al, J. Chem. Soc. 1956, 1622; or as disclosed in EP-A-146 269 or DE 2 944 295.

It will be evident that those compounds of formula (1), wherein $R_1$ is phenyl substituted by $C_1$-$C_5$alkanoyloxy, or wherein $R_6$ is a radical of formula —$CH_2$—$CO_2R_7$ or —$C_2H_4$—O—$R_8$, and $R_7$ is $C_1$-$C_{18}$alkyl and $R_8$ is $C_2$-$C_{19}$alkanoyl, can only be obtained in the above described manner with losses of yield, as these substituents are susceptible to hydrolysis. If it is desired to obtain suitable compounds, then it is advisable first to prepare derivatives derivatives by the novel process, wherein $R_1$ is hydroxy-substituted phenyl, and/or wherein $R_6$ is preferably a radical of formula —$CH_2CO_2H$ or —$C_2H_4$—OH. These derivatives can then be converted in a further step (d) in conventional manner into the desired ester or alkanoyloxy form by reaction with suitable alcohols or alkanoyl halides.

Attempts to effect the thiomethylation direct, i.e. avoiding the ring opening step (a), fail. They result in complex compound mixtures which have not been analysed in detail. However, the novel compounds are obtainable in good yield by carrying out the thiomethylation only after opening the lactone structure in the benzofuranone.

The novel compounds are very suitable for stabilising organic materials against thermal, oxidative and light-induced degradation.

Illustrative examples of such materials are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which may be crosslinked), for example high density polyethylene (HDPE), low density polyethylene (LDPE), linear low density polyethylene (LLDPE), branched low density polyethylene (BLDPE).

2. Mixtures of the polymers mentioned in 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/but-1-ene, propylene/butadiene, isobutylene/isoprene, ethylene/alkyl acrylates, ethylene/alkyl methacrylates, ethylene/vinyl acetate copolymers and their copolymers with carbon monoxide or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE/ethylene-vinyl acetate copolymers (EVA), LDPE/ethylene-acrylic acid copolymers (EAA), LLDPE/EVA, LLDPE/EAA and random or alternating polyalkylene/carbon monoxide-copolymers as well as mixtures thereof with other polymers, for example polyamides.

3a. Hydrocarbon resins (for example $C_5$–$C_9$) and hydrogenated modifications thereof (for example tackifiers) and mixtures of polyalkylenes and starch.

4. Polystyrene, poly(p-methylstyrene), poly($\alpha$-methylstyrene).

5. Copolymers of styrene or $\alpha$-methylstyrene with dienes or acrylic derivatives, such as, for example, styrene/butadiene, styrene/acrylonitrile, sterene/alkyl methacrylate, styrene/maleic anhydride, styrene/butadiene/alkyl acrylate, styrene/butadiene/alkyl methacrylate styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or $\alpha$-methylstyrene, for example styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed in 5), for example the copolymer mixtures known as ABS, MBS, ASA or AES polymers.

7. Halogen-containing polymers, such as polychloroprene, chlorinated rubbers, chlorinated or sulfochlorinated polyethylene, copolymers of ethylene and chlorinated ethylene, epichlorohydrin homo- and copolymers, polymers of halogenated vinyl compounds, for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from $\alpha,\beta$-unsaturated acids and derivatives thereof, such as polyacrylates and polymethacrylates, polymethyl methacrylate impact-modified with butyl acrylate, polyacrylamides and polyacrylonitriles.

9. Copolymers of the monomers mentioned in 8) with each other or with other unsaturated monomers, for example acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butral, polyallyl phthalate or polyallylmetlamine; as well as their copolymers with olefins mentioned in 1) above.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene and those polyoxymethylenes which contain ethylene oxide as comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes derived from polyethers, polyesters or polybutadienes with terminal hydroxyl groups on the one hand and aliphatic or aromatic polyisocyanates on the other, as well as precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides obtained by condensation of m-xylene, diamine and adipic acid; polyamides prepared from hexamethylenediamine and isophthalic acid and/or terephthalic acid and optionally an elastomer as modifier, for example poly(2,4,4-trimethylhexamethylene) terephthalamide or poly-m-phenylene isophthalamide. Further copolymers of the aforementioned polyamides with polyolefins, olefin copolymers, ionomers or chemically bonded or grafted elastomers; or with polyethers, as with polyethylene glycols, polypropylene glycols or polytetramethylene glycols. Polyamides or copolyamides modified with EPDM or ABS. Polyamides condensed during processing (RIM polyamide systems).

16. Polyureas, polyimides, polyamide-imides and polybenzimidazoles.

17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, polyhydroxybenzoates as well as block-copolyether-esters derived from polyethers having hydroxyl end groups; and also polyesters which are modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other, such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols and vinyl compounds as crosslinking agents, and also halogenated modifications thereof of low inflammability.

23. Thermosetting acrylic resins derived from substituted acrylic esters, such as epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers, such as cellulose, rubber, gelatin and chemically modified homologous derivatives thereof, such as cellulose acetates, cellulose propionates and cellulose butyrates, or the cellulose ethers, such as methyl cellulose; rosins and their derivatives.

27. Mixtures of polymers as mentioned above, for example PP/EPDM, polyamide/EPDM, or ABS, PVC/EVA, PVC/ABS, PVC/MBS, PC/ABS, PBTS/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

Further objects of the invention are thus also compositions comprising an organic material which is subject to oxidative, thermal or light-induced degradation and at least one compound of formula (1).

Preferred organic materials are polymers, typically synthetic polymers, preferably thermoplastic polymers. Especially preferred are polyolefins such as polypropylene or polyethylene.

To be singled out for special mention is the efficacy of the novel compounds against thermal and oxidative degradation, especially under the action of heat which occurs during the processing of thermoplasts. The novel compounds therefore have outstanding utility as heat stabilisers.

The compounds of formula (1) will preferably be added to the organic material to be stabilised in amounts of 0.0005 to 5% preferably 0.001 to 2%, typically 0.01 to 2%, based on the weight of said material.

In addition to comprising the compounds of formula (1), the inventive compositions may comprise further co-stabilisers, typically the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, 2,6-di-nonyl-4-methylphenol, 2,4-dimethyl-6-(1'-methyl-undec-1'-yl)phenol, 2,4-dimethyl-6-(1'-methyl-heptadec-1'-yl)phenol, 2,4-dimethyl-6-(1'-methyl-tridec-1'-yl)phenol and mixtures thereof.

1.2. Alkylthiomethylphenols, for example 2,4-dioctylthiomethyl-6-tert-butylphenol, 2,4-di-octylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-Di-tert-butyl-4-methoxyphenol, 2,5-di-tert-butyl-hydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxyphenyl)adipate.

1.4. Hydroxylated thiodiphenylethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl) dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)-pentane.

1.6. O-, N- and S-benzyl compounds, for example 3,5,3',5'-tetra(tert-butyl-4,4'-dihydroxydibenzyl) ether, octadecyl-4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.7. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis-(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazines, for example 2,4-bis[(octylmercapto-6-(3,5-di-tert-butyl-4-hydroxyanilino)]-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, di-octadecyl-5-tert-butyl-4-hydroxy-3-methylbenzylphosphonate, the calcium salt of monoethyl 3,5-di-tert-butyl-4-hydroxybenzylphosphonate.

1.11. Acylaminophenols, for example 4-hydroxylauryl anilide, 4-hydroxystearyl anilide, octyl N-(3,5-di-tertbutyl-4-hydroxyphenyl)carbamate.

1.12. Esters of β-(3,5-di-tertbutyl-4-hydroxyphenyl)-propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo-[2.2.2]octane.

1.13. Esters of β-(5-tert-butyl-4-hydroxy-3-methylphenyl)propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis(hydroxyethyl)oxalyl diamide, 3-thiaundecanol, 3-thiapentadecanol, trimethylhexanediol, trimethylolpropane, 4-hydroxymethyl-1-phospha-2,6,7-thioxabicyclo-[2.2.2]-octane.

1.14. Esters of β-(3,5-dicyclohexyl-4-hydroxyphenyl)propionic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and light stabilisers 2.1. 2-(2'-Hydroxyphenyl)benzotriazoles, for example the 5'-methyl-, 3',5'-di-tert-butyl-, 5'-tert-butyl-, 5'-(1,1,3,3-tetramethylbutyl), 5-chloro-3',5'-di-tert-butyl, 5-chloro-3'-tert-butyl-5'-methyl-, 3'-sec-butyl-5'-tert-butyl-, 4'-octyloxy-, 3',5'-di-tert-amyl- or 3',5'-bis(α,α-dimethylbenzyl)-mixture of 5-chloro-3'-tert-butyl-5'-(2-octyloxycarbonylethyl)- and 5-chloro-3'-tert-butyl-5'-[2-(2-ethylhexyloxy)-carbonylethyl]-, 5-chloro-3'-tert-butyl-5'-(2-methoxycarbonylethyl)-, 3'-tert-butyl-5'-(2-methoxycarbonylethyl)-, 3'-tert-butyl-5'-(2-octyloxycarbonylethyl)-, 3'-tert-butyl-5'-[2-(2-ethylhexyloxy)-carbonylethyl]-, 3'-dodecyl-5'-methyl- and 3'-tert-butyl-5'-(2-isooctyloxycarbonylethyl)-2'-hydroxyphenyl-2H-benzotriazol-2-yl, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$, wherein R=3'-tert-butyl-4'-hydroxy-5'-2H-benzotriazol-2-ylphenyl.

2.2. 2-Hydroxybenzophenonee, for example the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative.

2.3. Esters of unsubstituted or substituted benzoic acids, for example 4-tertbutylphenyl salicylate, phenyl salicylate, octylphenyl salicylate, dibenzoyl resorcinol, bis(4-tert-butylbenzoyl) resorcinol, benzoyl resorcinol, the 2,4-di-tertbutylphenyl ester of 3,5-di-tert-butyl-4-hydroxybenzoic acid, hexadecyl 3,5-di-tert-butyl-4-hydroxybenzoate, octadecyl 3,5-di-tert-butyl-4-hydroxybenzoate, the 2-methyl-4,6-di-tert-butylphenyl ester of 3,5-di-tert-butyl-4-hydroxybenzoic acid.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1- or 1:2 complex, with or without additional ligands, as n-butylamine, triethanolamine or N-cyclohexyl-diethanolamine, nickel dibutyl dithiocarbamate, nickel salts of monoalkyl esters of 4-hydroxy-3,5-di-tert-butylbenzylphosphonic acid, as of methyl or ethyl esters, nickel complexes of ketoximes, as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, the bis(1,2,2,6,6-pentamethylpiperidyl) ester of n-butyl-3,5-di-tert-butyl-4-hydroxybenzylmalonic acid, the condensate of 1-hydroxyethyl-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-s-triazine, tris(2,2,6,6-tetramethyl-4-piperidyl)-nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5- triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxy-propoxy)phenyl]-4,6-bis(2,4-dimethylphenyl)-1,3,5-triazine, 2-[2-hydroxy-4-(2-hydroxy-3-octyloxy-propoxy)-phenyl]-4,6-bis(2,4-dimethylphenyl)-1,3,5-triazine.

.3. Metal deactivators, for example N,N'-diphenyloxamide, N-salicylal-N'-salicyloylhydrazine, N,N'-bis(-salicyloyl)hydrazine, N,N'-bis(3,5-di-tertbutyl-4-hydroxyphenylpropionyl)hydrazine, 3-salicyloylamino-1,2,4-triazole, bis(benzylidene)oxalic dihydrazide, oxanilide, isophthalic dihydrazide, sebacic bis(phenylhydrazide), N,N'-diacetaladipic dihydrazide, N,N'-bis(-salicyloyl)oxalic dihydrazide, N,N'-bis(salicyloyl)thiopropionic dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, bis(2,6-di-tert-butyl-4-methylphenyl)pentaerythritol diphosphite, bis(isodecyloxy)pentaerythritol diphosphite, bis(2,4-di-tert-butyl-6-methylphenyl)pentaerythritol diphosphite, bis(2,4,6-tri-tert-butylphenyl)pentaerythritol diphosphite, tristearysorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocine.

5. Compounds which decompose peroxide, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dycyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibers, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

The co-stabilizers are typically used in concentrations of 0.01 to 10%, based on the total weight of the material to be stabilised.

The compounds of formula (1) and other optional additives are incorporated into the organic polymer by known methods, conveniently before or during shaping to moulded articles or alternatively by coating the organic polymers with a solution or dispersion of the compounds and subsequently evaporating the solvent. The compounds of formula (1) can also be added to the materials to be stabilised in the form of a masterbatch which contains these compounds, typically in a concentration of 2.5 to 25% by weight.

The compounds of formula (1) can also be added before or during polymerisation or before crosslinking.

The compounds of formula (1) can be incorporated into the organic polymer in pure form or in waxes, oils or polymer encapsulations.

The compounds of formula (1) can also be sprayed on to the polymer to be stabilised. They are able to dilute other additives (typically the conventional additives listed above) or melts thereof, so that they can also be sprayed together with these additives on to the polymer to be stabilised. Application by spraying during deactivation of the polymerisation catalysts is especially advantageous, in which case spraying is conveniently effected with the vapour used for deactivation.

It may be expedient to spray the compounds of formula (1), with or without other additives, on to spherical polymerised polyolefins.

The stabilised materials may be in any form of presentation, typically sheets, filaments, ribbons, mouldings, profiles or binders for coating compositions, adhesives or putties.

As already emphasised, the novel compounds are used with particular advantage as stabilisers in polyolefins, preferably as heat stabilisers. Excellent stabilisation is achieved when the compounds are used in conjunction with organic phosphites or phosphonites. The novel compounds have in this case the advantage that they are effective in exceedingly low concentration, typically of 0.0001 to 0.015% by weight, preferably of 0.0001 to 0.008% by weight, based on the polyolefin. The organic phosphite or phosphonite is conveniently used in a concentration of 0.01 to 2% by weight, preferably of 0.01 to 1% by weight, based on the polyolefin. It is preferred to use the organic phosphites and phosphonites disclosed in German patent application P 4202276.2. Attention is drawn in particular to the claims, to the Examples and to pages 5, last paragraph, to 11. Particularly suitable phosphites and phosphonites will also be found under item 4 of the above list of co-stabilisers.

The invention is illustrated in more detail by the following Examples in which parts and percentages are by weight.

PREPARATION OF THE COMPOUNDS OF FORMULA (1)

Example 1

42.05 g of 3-phenylbenzofuran-2-one are added to 200 ml of 2N NaOH in water and the mixture is heated for 30 minutes at reflux. To the homogeneous solution are added 47.2 ml of benzyl mercaptan, 24 g of paraformaldehyde and 4.3 ml of dimethylamine (40% in water), and the reaction mixture is boiled for 17 hours under nitrogen. After cooling, the reaction mixture is acidified with 233 ml of 2N HCl and then heated once more to reflux temperature. The reaction mixture is then extracted with toluene (3×100 ml), the extracts are washed with water, dried over magnesium sulfate and concentrated by evaporation. Crystallisation from toluene/hexane gives 57.5 g of compound 121 listed in Table 1.

The other compounds listed in Table 1 can also be prepared in accordance with the same general procedure.

TABLE 1

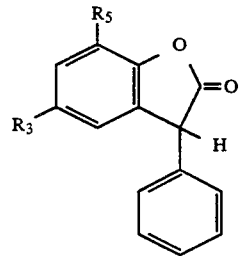

| No. | $R_5$ | $R_3$ | m.p. (°C.) | Yield (%) | C calcd (%) | H | S found (%) |
|---|---|---|---|---|---|---|---|
| 101 | $C_8H_{17}SCH_2-$ | $CH_3-$ | 39–40 | 48 | 75.35 | 7.90 | |
| | | | | | 75.18 | 7.98 | |
| 102 | $C_{12}H_{25}SCH_2-$ | $CH_3-$ | 59–62 | 36 | 76.67 | 8.73 | |
| | | | | | 76.65 | 8.79 | |
| 103 | $C_6H_5SCH_2-$ | $CH_3-$ | 79–82 | 32 | 76.27 | 5.24 | 9.25 |
| | | | | | 76.34 | 5.19 | 8.80 |
| 104 | $C_6H_5CH_2SCH_2-$ | $CH_3-$ | 75–78 | 41 | 76.64 | 5.59 | 8.89 |
| | | | | | 76.88 | 5.65 | 8.84 |
| 105** | $HOCH_2CH_2SCH_2-$ | $CH_3$ | Oel | 45 | characterised by $^1$H-NMR: $\delta(H) = 4.87$ ppm | | |
| 106** | $C_8H_{17}SCH_2-$ | t-butyl | oil | 60 | characterised by $^1$H-NMR: $\delta(H) = 4.89$ ppm | | |
| 107** | $C_{12}H_{25}SCH_2-$ | t-butyl | oil | 72 | characterised by $^1$H-NMR: $\delta(H) = 4.89$ ppm | | |
| 108** | $C_6H_5SCH_2-$ | t-butyl | 79–82 | 11 | characterised by $^1$H-NMR: $\delta(H) = 4.85$ ppm | | |
| 109 | $C_6H_5CH_2SCH_2-$ | t-butyl | resin | 67 | 77.58 | 6.51 | 7.96 |
| | | | | | 77.54 | 6.60 | 7.87 |
| 110** | $HOCH_2CH_2SCH_2-$ | t-butyl | resin | 51 | characterised by $^1$H-NMR: $\delta(H) = 4.90$ ppm | | |
| 111** | $HO_2CCH_2SCH_2-$ | t-butyl | resin | 48 | characterised by $^1$H-NMR: $\delta(H) = 4.89$ ppm | | |
| 112* | $^1ACO_2(CH_2)_2SCH_2-$ | t-butyl | oil | 93 | 75.20 | 9.39 | |
| | | | | | 75.14 | 9.38 | |
| 113* | $^2BO_2CCH_2SCH_2-$ | t-butyl | 32–50 | 30 | 75.20 | 9.39 | 5.15 |
| | | | | | 75.22 | 9.43 | 5.45 |
| 114 | $C_{12}H_{25}SCH_2-$ | $C_6H_5-$ | 73–77 | 41 | 79.16 | 8.05 | |
| | | | | | 79.10 | 8.25 | |
| 115 | $C_6H_5CH_2SCH_2-$ | $C_6H_5-$ | 94–98 | 41 | 79.59 | 5.25 | 7.59 |
| | | | | | 79.51 | 5.15 | 7.37 |
| 116** | $CH_3-$ | $C_{12}H_{25}SCH_2-$ | 32–35 | 44 | characterised by $^1$H-NMR: $\delta(H) = 4.88$ ppm | | |
| 117** | t-butyl | $C_{12}H_{25}SCH_2-$ | oil | 69 | characterised by $^1$H-NMR: $\delta(H) = 4.70$ ppm | | |
| 118** | t-butyl | $C_6H_5CH_2SCH_2-$ | oil | 69 | characterised by $^1$H-NMR: $\delta(H) = 4.81$ ppm | | |
| 119 | $C_8H_{17}SCH_2-$ | $C_8H_{17}SCH_2-$ | oil | 65 | 72.95 | 8.80 | 12.17 |
| | | | | | 72.97 | 8.84 | 12.19 |
| 120 | $C_{12}H_{25}SCH_2-$ | $C_{12}H_{25}SCH_2-$ | 44–46 | 38 | 75.18 | 9.78 | |
| | | | | | 75.22 | 9.83 | |
| 121 | $C_6H_5CH_2SCH_2-$ | $C_6H_5CH_2SCH_2-$ | 73–75 | 53 | 74.66 | 5.43 | 13.28 |

TABLE 1-continued

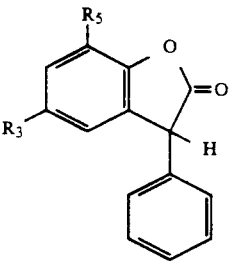

| No. | R₅ | R₃ | m.p. (°C.) | Yield (%) | C calcd (%) | H | S | | found (%) | |
|---|---|---|---|---|---|---|---|---|---|---|
| | | | | | 74.54 | 5.39 | 13.22 | | | |
| 122 | | (structure) | 65-68 | 53 | 78.44 | 8.07 | 6.75 | | | |
| | | | | | 78.31 | 8.26 | 6.92 | | | |

[1] A = C₁₇H₃₅
[2] B = C₁₈H₃₇
*Both compounds are obtained by subsequent esterification (q.v. Example 2).
**The chemical displacements were measured by samples dissolved in CDCl₃.

Example 2

7.13 g of compound (110) and 6.7 g of stearoyl chloride are heated in 20 ml of toluene for 4 hours to 100° C. The mixture is cooled and then washed with water, sodium bicarbonate solution and again with water, dried over magnesium sulfate and concentrated by evaporation. Chromatography of the residue over silica gel (dichloromethane/hexane 9:1) gives 11.6 g of oily compound (112).

Compound (113) is obtained by esterifying compound (111) with stearyl alcohol in the presence of p-toluenesulfonic acid in per se known manner.

Example 3 a) Preparation of compound (123):

13.4 g of 3-(4-ethoxyphenyl)-5-methylbenzofuran-2-one are dissolved under nitrogen at 90° C. in 100 ml of 1N sodium hydroxide solution. Then 3.0 g of paraformaldehyde, 7.5 g of n-octane-1-thiol and 1.2 ml of dimethylamine (in the form of a 40% solution in water) are added and the whole mixture is boiled under nitrogen for 22 hours. Afterwards the reaction mixture is acidified with 60 ml of 2N hydrochloric acid and then extracted with 2×50 ml of toluene. The extracts are dried over magnesium sulfate and concentrated by evaporation. The residue is recrystallised twice from acetonitrile, giving 11.8 g (55%) of compound (123), m.p. 70°-73° C. Analysis: calcd.: 73.20% C; 8.03% H; 7.51% S; found: 73.15% C; 8.16% H; 7.74% S.

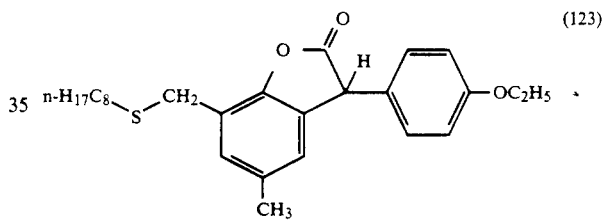

b) Preparation of the starting 3-(4-ethoxyphenyl)-5-methylbenzofuran-2-one:

A mixture of 162 g (1.50 mol) of 4-methylphenol and 196.2 g (1.0 mol) of 4-ethoxymandelic acid are stirred under nitrogen for 2 hours at 140°-150° C. Stirring is then continued for 1.5 hours at 150° C. under a slight vacuum (50 mbar). Excess 4-methoxyphenol is removed by distillation under a high vacuum. Crystallisation of the residue from xylene/ethanol yields 204 g (76%) of 3-(4-ethoxyphenyl)-5-methylbenzofuran-2-one of m.p. 82°-86° C.

Example 4 a) Preparation of compound (124):

Following the general procedure described in Example 3, compound (124) is obtained from 3-(3,5-dimethyl-4-methoxyphenyl)benzofuran-2-one and with twice the amount of paraformaldehyde, benzyl mercaptan and dimethylamine. Purification over silica gel with the solvent system dichloromethane/hexane 3:2 gives the compound (124) as an oil in a yield of 35%. Analysis: calcd.: 73.30% C; 5.97% H; 11.86% S; found: 73.23% C; 5.99% H; 11.82% S.

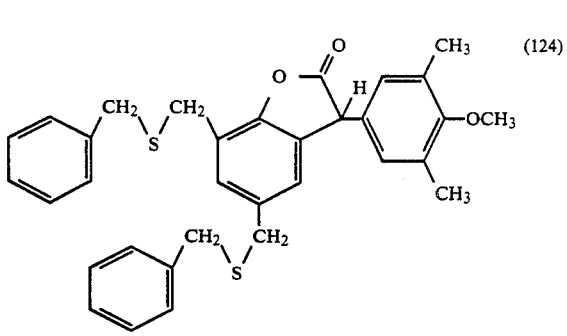

(124)

b) Preparation of the starting 3-(3,5-dimethyl-4-methoxyphenyl)benzofuran-2-one:

Following the general procedure described in Example 3b, 3-(3,5-dimethyl-4-methoxyphenyl)benzofuran-2-one of m.p. 122°-125° C. is prepared from phenol and 3,5-dimethyl-4-methoxymandelic acid.

Example 5

Stabilisation of polyethylene during processing 100 parts of polyethylene powder (Lupolen ®5260 Z) are blended with 0.05 part of pentaerythritol tetrakis[3-(3,5-di-tert-butyl-4-hydroxyphenyl)propionate], 0.05 part of tris(2,4-di-tert-butylphenyl)phosphite and 0.05 part of a stabiliser of Table 1 and the blend is kneaded in a Brabender plastograph at 220° C. and 50 rpm. During this time the kneading resistance is recorded continuously as torque. In the course of the kneading time the polymer begins to crosslink after prolonged constancy, as can be determined by the rapid increase in torque. The time taken until a marked increase in torque is shown in Table 2 as a measure of the stabilising action.

TABLE 2

| Compound | Time until increase in torque (min) |
| --- | --- |
| — | 12 |
| 102 | 16 |
| 107 | 15 |
| 110 | 19 |
| 112 | 18 |
| 114 | 19 |
| 115 | 16 |
| 116 | 19.5 |
| 117 | 18.5 |
| 118 | 16.5 |
| 119 | 17 |
| 120 | 15 |
| 122 | 18.5 |

What is claimed is:

1. A compound of formula (1)

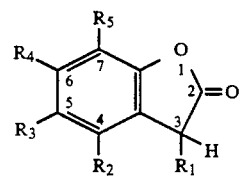

wherein $R_1$ is phenyl or phenyl which is substituted by $C_1$-$C_{18}$alkyl, $C_1$-$C_{18}$alkoxy, $C_3$-$C_{18}$alkenyloxy, benzyloxy, $C_1$-$C_{18}$alkanoyloxy, hydroxy or halogen, $R_2$ and $R_4$ are each independently of the other hydrogen or $C_1$-$C_4$alkyl, or $R_4$ and $R_5$, together with the linking carbon atoms, form a phenyl ring, and $R_3$ and $R_5$ are each independently of the other a radical of formula —$CH_2$—S—$R_6$, wherein $R_6$ is $C_1$-$C_{18}$alkyl, $C_5$-$C_8$cycloalkyl, benzyl, phenyl or a radical of formula —$CH_2$—$CO_2R_7$ or —$C_2H_4$—O—$R_8$, wherein $R_7$ is hydrogen or $C_1$-$C_{18}$alkyl and $R_8$ is hydrogen or $C_2$-$C_{19}$alkanoyl.

2. A compound according to claim 1, wherein $R_1$ is phenyl or phenyl which is substituted by $C_1$-$C_4$alkyl, $C_1$-$C_4$alkoxy, hydroxy, $C_1$-$C_5$alkanoyloxy or halogen.

3. A compound according to claim 1, wherein $R_1$ is phenyl or phenyl which is substituted by $C_1$-$C_4$alkyl, $C_1$-$C_4$alkoxy, $C_3$-$C_4$alkenyloxy, benzyloxy, hydroxy, $C_1$-$C_5$alkanoyloxy or chloro.

4. A compound according to claim 1, wherein $R_3$ and $R_5$ are each independently of the other a radical of formula —$CH_2$—S—$R_6$, wherein $R_6$ is $C_8$-$C_{18}$alkyl, cyclohexyl, benzyl, phenyl, a radical of formula —$CH_2$—$CO_2R_7$, wherein $R_7$ is $C_{12}$-$C_{18}$alkyl, or a radical of formula —$C_2H_4$—O—$R_8$, wherein $R_8$ is hydrogen or $C_{13}$-$C_{19}$alkanoyl.

5. A compound according to claim 1, wherein $R_3$ and $R_5$ are each independently of the other a radical of formula —$CH_2$—S—$R_6$, wherein $R_6$ is $C_8$-$C_{12}$alkyl or benzyl.

6. A composition comprising
   α) an organic material which is subject to oxidative, thermal or light-induced degradation, and
   β) at least one compound of formula (1) according to claim 1.

7. A composition according to claim 6, wherein component α) is a synthetic polymer.

8. A composition according to claim 6, which contains component β) in an amount of 0.0005 to 5% by weight, based on the weight of component α).

9. A composition according to claim 6, which additionally comprises an organic phosphite or phosphonite.

10. A composition according to claim 6, which additionally comprises a phenolic antioxidant.

11. A process for stabilising an organic material against oxidative, thermal or light-induced degradation, which comprises incorporating therein or applying thereto at least one compound as claimed in claim 1.

12. A compound according to claim 1 wherein $R_1$ is phenyl or phenyl which is substituted by $C_1$-$C_4$alkyl or $C_1$-$C_4$alkoxy, $R_2$ and $R_4$ are hydrogen or $R_4$ and $R_5$, together with the linking carbon atoms, form a phenyl ring, and $R_3$ and $R_5$ are independently of the other a radical of formula —$CH_2$—S—$R_6$, wherein $R_6$ is $C_8$-$C_{12}$alkyl, benzyl, phenyl, a radical of formula —$CH_2$—$CO_2R_7$, wherein $R_7$ is hydrogen or $C_{12}$-$C_{18}$alkyl, or a radical of formula —$C_2H_4$—O—$R_8$, wherein $R_8$ is hydrogen or $C_{13}$-$C_{19}$alkanoyl.

* * * * *